(12) United States Patent
Linares et al.

(10) Patent No.: US 9,827,406 B2
(45) Date of Patent: Nov. 28, 2017

(54) INSERTION TOOL FOR IMPLANTING A MEDICINAL DELIVERY DEVICE UPON AN INTERNAL ORGAN

(71) Applicants: Miguel A. Linares, Bloomfield Hills, MI (US); Elie Mulhem, Troy, MI (US)

(72) Inventors: Miguel A. Linares, Bloomfield Hills, MI (US); Elie Mulhem, Troy, MI (US)

(*) Notice: Subject to any disclaimer, the term of this patent is extended or adjusted under 35 U.S.C. 154(b) by 194 days.

(21) Appl. No.: 14/820,149

(22) Filed: Aug. 6, 2015

(65) Prior Publication Data

US 2015/0335868 A1    Nov. 26, 2015

Related U.S. Application Data

(62) Division of application No. 14/047,409, filed on Oct. 7, 2013, now abandoned.

(60) Provisional application No. 61/710,079, filed on Oct. 5, 2012.

(51) Int. Cl.
*A61M 31/00* (2006.01)
*A61K 9/00* (2006.01)
*A61M 25/02* (2006.01)
*A61M 25/04* (2006.01)

(52) U.S. Cl.
CPC ......... *A61M 31/002* (2013.01); *A61K 9/0036* (2013.01); *A61M 25/02* (2013.01); *A61M 25/04* (2013.01); *A61M 2202/0007* (2013.01); *A61M 2205/04* (2013.01); *A61M 2210/14* (2013.01)

(58) Field of Classification Search
CPC .. A61K 9/0034; A61K 9/0036; A61K 9/0039; A61M 37/0069; A61M 37/0015; A61M 31/007; A61F 6/12; A61F 6/18
See application file for complete search history.

(56) References Cited

U.S. PATENT DOCUMENTS

| | | | | |
|---|---|---|---|---|
| 862,712 | A * | 8/1907 | Collins | A61F 6/18 128/840 |
| 2,008,380 | A * | 7/1935 | Bachmann | A61F 6/12 128/838 |
| 2,818,856 | A * | 1/1958 | Kohl | A61F 6/12 128/838 |
| 3,794,044 | A * | 2/1974 | Vennard | A61B 17/442 606/123 |
| 4,144,317 | A | 3/1979 | Higuchi et al. | |
| 4,309,996 | A | 1/1982 | Theeuwes | |
| 5,228,451 | A * | 7/1993 | Bales | A61B 10/06 600/564 |
| 5,271,385 | A * | 12/1993 | Bailey | A61B 17/0218 600/214 |

(Continued)

*Primary Examiner* — Kevin C Sirmons
*Assistant Examiner* — William Carpenter
(74) *Attorney, Agent, or Firm* — Dinsmore & Shohl LLP

(57) ABSTRACT

An insertion tool for implanting a medicinal delivery device, such as which is attached to the tissue or mucous membrane lining of a human organ, such as a female cervix, through a variety of means not limited to vacuum suction and/or mechanical fastening. The delivery tool exhibits an elongated body with a vacuum inducing support surface for retaining the delivery device in a first implantation stage. Forward end located actuating clamps grip peripheral locations of the device during implantation, and upon completion, can be pivoted out of engagement with the body of the delivery device, via the toggle initiated displacement of a sleeve integrated into the elongated body.

5 Claims, 14 Drawing Sheets

(56) References Cited

U.S. PATENT DOCUMENTS

| | | | |
|---|---|---|---|
| 5,527,313 A * | 6/1996 | Scott | A61B 17/2909 606/41 |
| 5,773,019 A | 6/1998 | Ashton et al. | |
| 6,159,152 A * | 12/2000 | Sumanaweera | A61B 8/14 600/443 |
| 6,569,201 B2 | 5/2003 | Moumene et al. | |
| 6,726,920 B1 | 4/2004 | Theeuwes et al. | |
| 6,808,506 B2 | 10/2004 | Lastovich et al. | |
| 6,878,137 B2 | 4/2005 | Benchetrit | |
| 6,957,813 B2 * | 10/2005 | Verstraeten | A63F 9/30 273/448 |
| 7,195,774 B2 | 3/2007 | Carvalho et al. | |
| 8,216,177 B2 | 7/2012 | Heruth et al. | |
| 8,538,515 B2 | 9/2013 | Atanasoska et al. | |
| 8,986,326 B2 * | 3/2015 | Satake | A61B 17/08 606/142 |
| 2001/0037117 A1 | 11/2001 | Gambale et al. | |
| 2004/0087893 A1 * | 5/2004 | Kwon | A61B 17/205 604/46 |
| 2005/0118388 A1 | 6/2005 | Kingsford | |
| 2008/0195035 A1 * | 8/2008 | Frederickson | A61K 9/0021 604/22 |
| 2008/0269670 A1 | 10/2008 | Kingsford | |
| 2009/0274746 A1 | 11/2009 | Gupta et al. | |
| 2010/0094256 A1 * | 4/2010 | Kassab | A61K 9/0024 604/514 |
| 2010/0256568 A1 | 10/2010 | Frederickson et al. | |
| 2010/0331775 A1 | 12/2010 | Atanasoska et al. | |
| 2011/0152606 A1 * | 6/2011 | Bollinger | A61B 17/43 600/35 |
| 2012/0020877 A1 | 1/2012 | Raspagliesi | |
| 2012/0071905 A1 | 3/2012 | Girard et al. | |
| 2012/0179172 A1 * | 7/2012 | Paul, Jr. | A61B 17/0057 606/142 |
| 2013/0144250 A1 | 6/2013 | Schwarz et al. | |

* cited by examiner

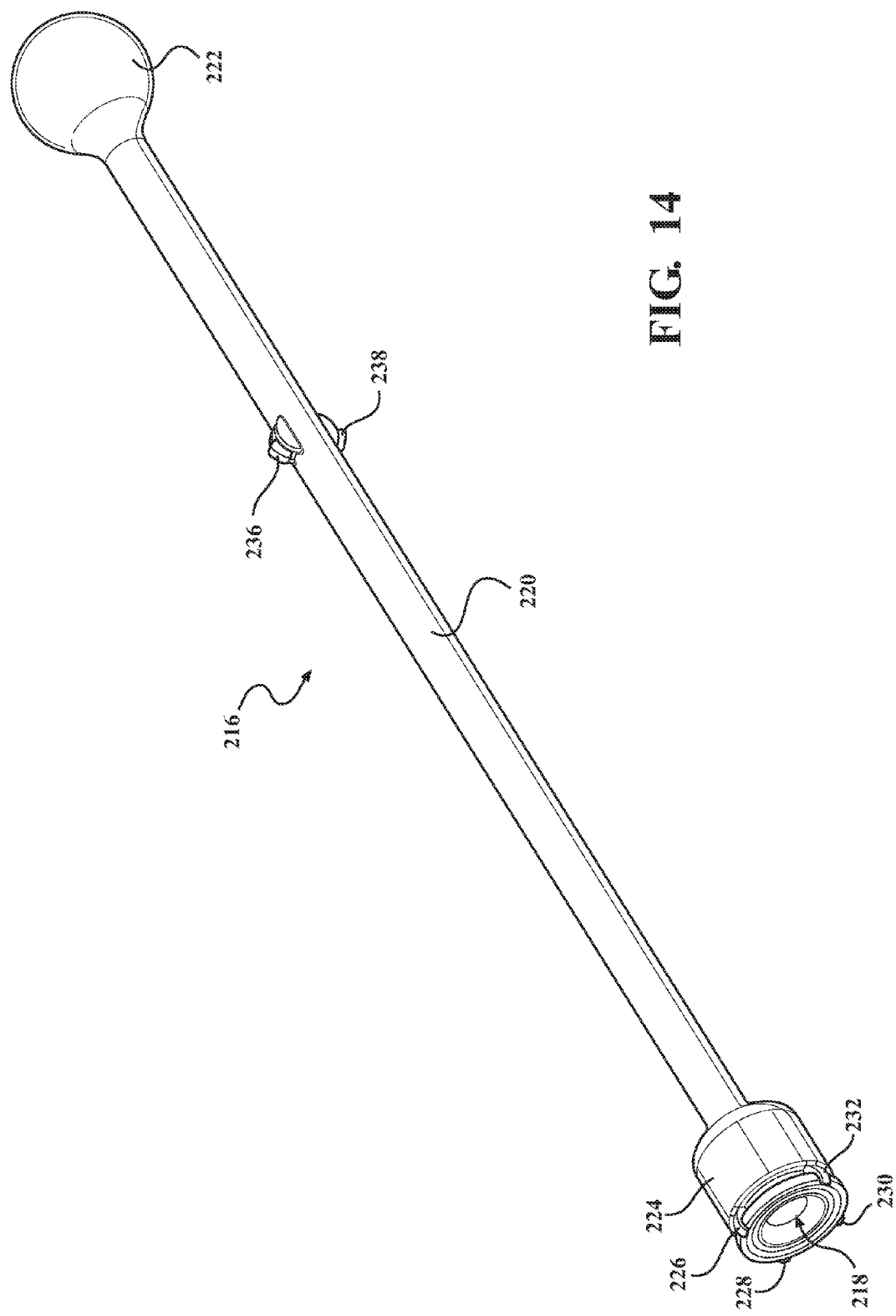

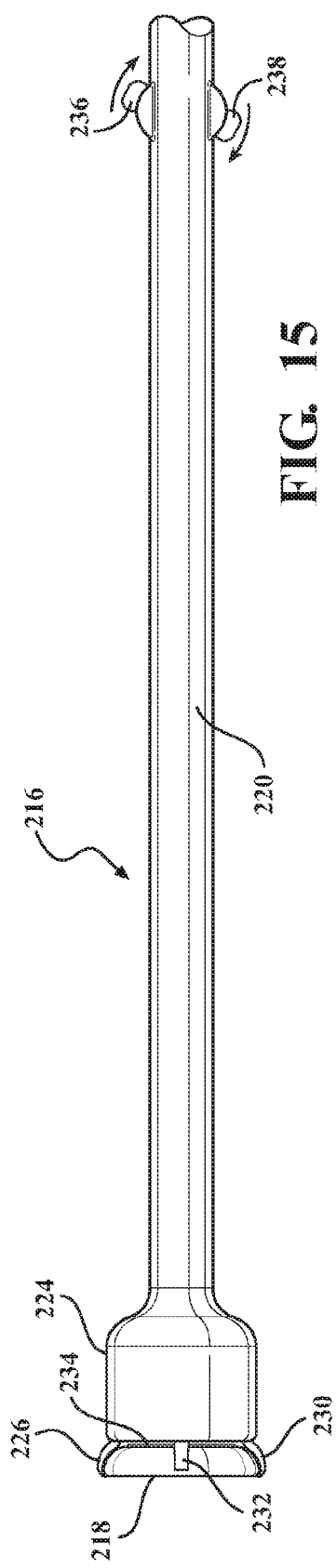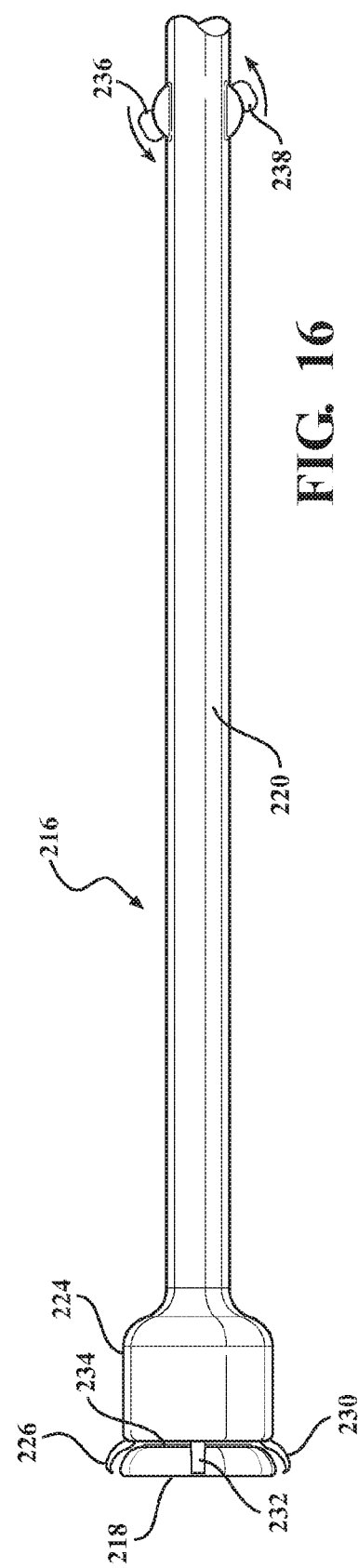

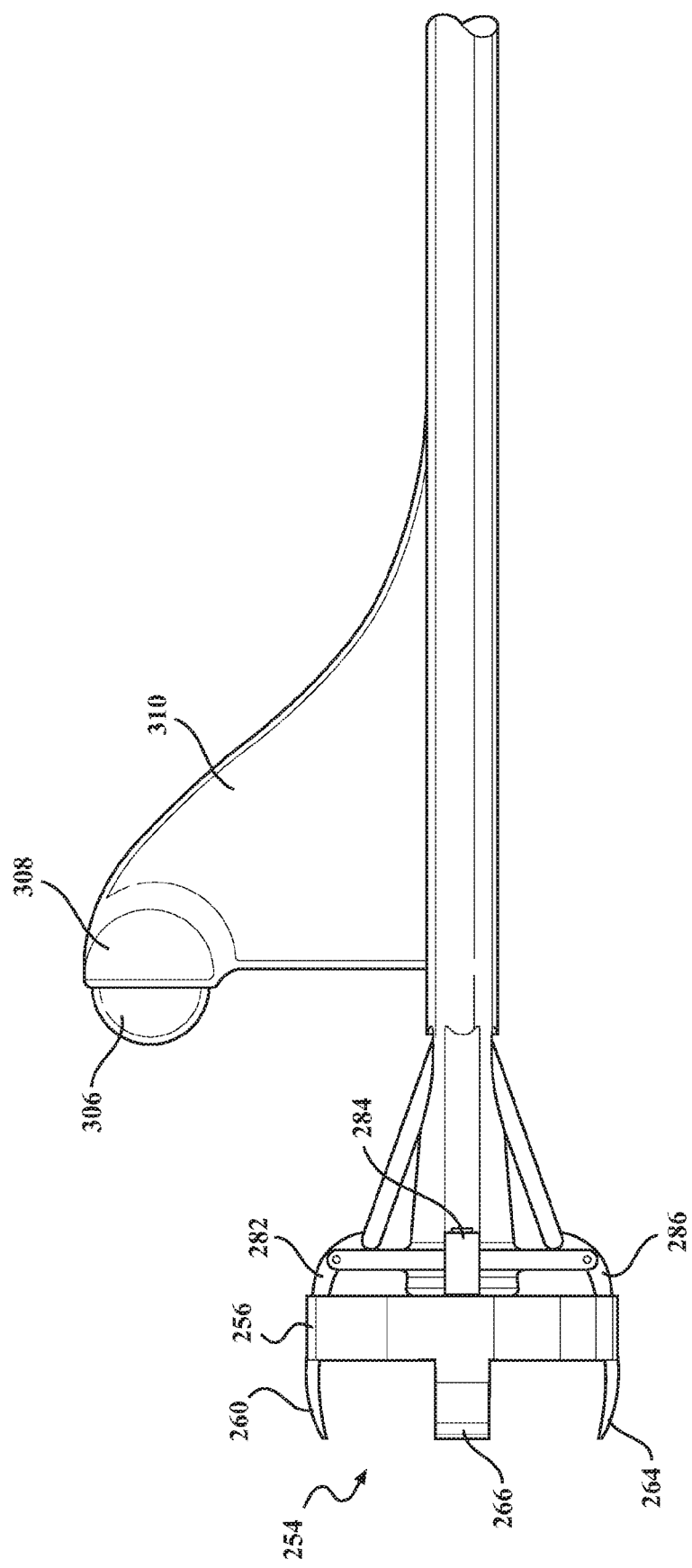

INSERTION TOOL FOR IMPLANTING A MEDICINAL DELIVERY DEVICE UPON AN INTERNAL ORGAN

CROSS-REFERENCE TO RELATED APPLICATIONS

This application is a Continuation in Part of application Ser. No. 14/047,409 filed on Oct. 7, 2013. Application Ser. No. 14/047,409 claims the benefit of U.S. Provisional Application 61/710,079 filed on Oct. 5, 2012, the contents of which are incorporated herein in their entirety.

FIELD OF THE INVENTION

The present invention is generally related to an area focused medicinal delivery system associated with human internal organs. More specifically, the present invention discloses an insertion tool for implanting a medicinal delivery device, such as which is attached to the tissue or mucous membrane lining of a human organ, such as a female cervix, through a variety of means not limited to vacuum suction and/or mechanical fastening.

BACKGROUND OF THE INVENTION

The prior art is documented with examples of medicinal delivery devices, such as which can be implanted in situ within a patient body cavity. Examples of such implantable drug delivery devices include each of Atanasoska et al., U.S. Pat. No. 8,538,515, Heruth et al. U.S. Pat. No. 8,216,177, Aston U.S. Pat. No. 5,773,019 and Benchetrit U.S. Pat. No. 6,878,137.

An example of a uterine attachable and implantable device is depicted in Girard 2012/0071905 which teaches a biocompatible polyethylene teraphathalate (PET) material which is deliverable into the body cavity and which contains a tissue growth promoting attribute for reducing or stopping excessive bleeding. Another example of an implantable and sealable system for unidirectional delivery of therapeutic agents to tissues is depicted in U.S. Pat. No. 7,195,774 to Carvalho. The implantable device includes a tissue or organ surface contacting port or window for permitting diffusion of the agent, such as chemotherapeutics or bio-active agents.

US 2012/0020877 to Raspagliesi teaches an intrauterine device for local release of drugs in the loco-regional treatment of tumors of the uterine cervix which includes an elongate stem positioned in the cervix canal. The stem consists of an inner hollow core and a coating containing a gradual-release drug. The stem is attached to a first upper end located element for blocking the stem inside the uterine cavity and a second lower end located element at the ectocervix location of the vagina.

SUMMARY OF THE INVENTION

The present invention discloses an insertion tool for implanting an implantable device, such as which is attached to the tissue or mucous membrane lining of a human organ, such as further by example a female cervix, through a variety of means not limited to vacuum suction and/or mechanical fastening. The delivery tool exhibits an elongated body with a vacuum inducing support surface for retaining the delivery device in a first implantation stage. Forward end located actuating clamps grip peripheral locations of the device during implantation, and upon completion, can be pivoted out of engagement with the body of the delivery device, via the toggle initiated displacement of an inner sleeve integrated into the elongated body.

BRIEF DESCRIPTION OF THE DRAWINGS

Reference will now be made to the attached drawings, when read in combination with the following detailed description, wherein like reference numerals refer to like parts throughout the several views, and in which:

FIG. 14 is a perspective illustration of an insertion tool for delivery and implanting a medicinal delivery device;

FIG. 15 is a plan view of the tool of FIG. 14 and depicting a handle supported trigger mechanism for manipulating a combination of perimeter clamping and suctioning aspects for supporting the medicinal delivery device upon the inserting end of the tool, such as during the tool end and device being located in situ within the patient for subsequent depositing of the medicinal delivery device;

FIG. 16 is a successive view to FIG. 15 and depicting actuation of the trigger mechanism for releasing the medicinal delivery device;

FIG. 23 is an illustration of a modified inserting end of an installation tool such as similar to that depicted in FIG. 20 and in which a high intensity light source is integrated at a narrow cross sectional and elevated location in order to facilitate correct location and delivery of the medicinal delivery device.

DETAILED DESCRIPTION OF THE PREFERRED EMBODIMENTS

As previously described, the present invention discloses an implantable device which is attachable to the tissue or membrane lining of a human organ, such as a female cervix, through a variety of means not limited to vacuum suction and/or mechanical fastening. The implantable device, as further described in detail with reference to each of the successive embodiments, incorporates a medicinal holding component which is configured for delivering, in controlled and time release fashion, an on-site medication, such as an anti-cancer or other disease treating composition, incorporated within the component prior to implantation.

As is known, the uterus (also commonly referred to as "womb") is a major female hormone-responsive and reproductive sex organ possessed by most mammals including humans. In the human anatomy, one of the uterus parts, called the cervix, open into the vagina, while the other is connected to one or both fallopian tubes. As is further known, it is within the uterus that a fetus develops during gestation, this usually developing completely in placental mammals including humans.

The uterus typically includes a plurality of layers, from inside to outside including each of the endometrium (inner lining of the uterine cavity), the myometrium (smooth muscle layer), the parametrium (loose connective tissue around the uterus), and perimetrium (peritoneum covering of the fundus and ventral and dorsal aspects of the uterus). For purposes of simplification in association with the subsequent detailed description of each of the medicinal delivery devices associated with the inventions, the multiple layers recited herein will be generally referred to as the "uterine wall".

Additional anatomical aspects of the uterus include the provision of ligaments, also terms endopelvic fascia, for holding it into position within the pelvis. Types of these ligaments further include such as the cardinal and pubocervical (sides of cervix), transverse, cervical and uterosacral (posterior cervix) ligaments. Additional to its normal sexual reproductive functions, the uterus is susceptible to various medical risks or conditions, these often resulting from the carrying of a fetus and including such as various pathological changes in the position of the uterus (such as associated with tearing or damage to the uterine wall and associate ligament structure). Other conditions associated with the uterus include the formation of carcinomas (malignant tumors or growths), fibroids, adenomyosis, pyometra, uterine malformations, as well as Asherman's syndrome.

Figure 1:
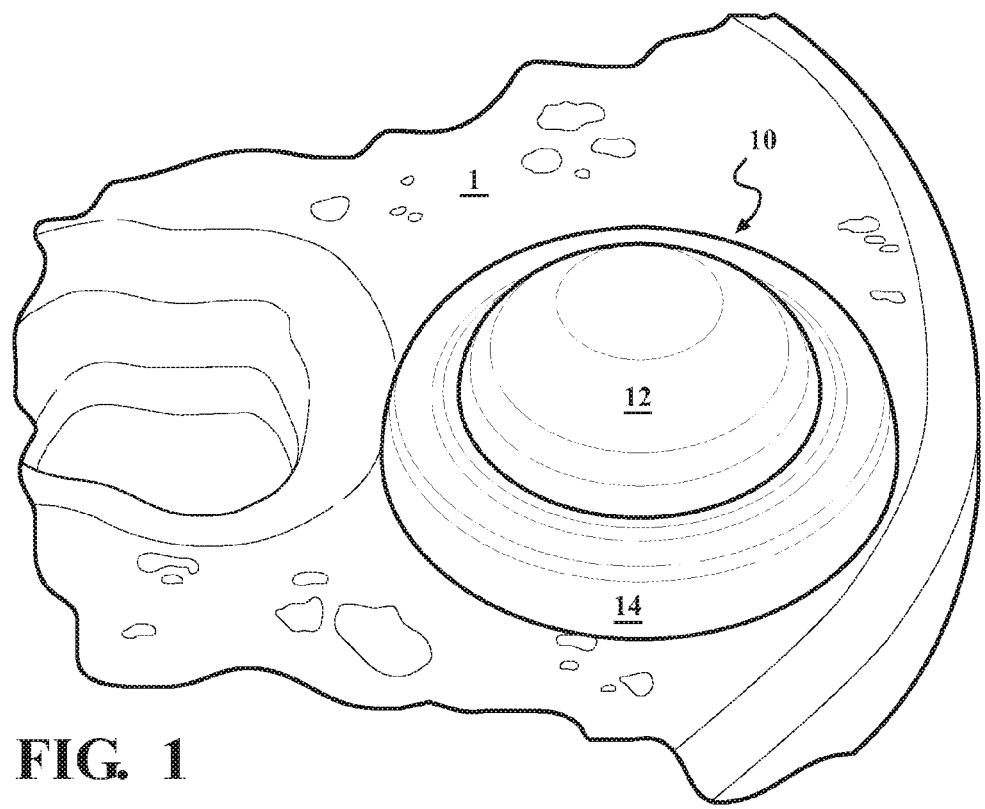
FIG. 1 is an enlarged and environmental perspective of a human uterus to which the medicinal delivery device is secured at a surface location by a depressible and suction inducing middle component.

In view of the above description, and referring initially to FIG. 1, an enlarged environmental perspective is shown of a human cervix 1 to which a medicinal delivery device, generally at 10, is secured at a surface location. The delivery device 10 exhibits, in one non-limiting configuration, a depressible and suction inducing middle component 12 constructed of a soft and easily deformable plastic along with an outer and suction maintaining annular skirt 14 which is usually constructed of a somewhat more durable and less flexible polymer or polymer composite.

As is known, the exterior surface of the cervix exhibits a very moist consistency which is particularly amenable to retaining in location an exteriorly suction attachable component as is provided by the device 10. Referring to the rotated underside in FIG. 2 of the medicinal delivery device 10, additionally illustrated is the concentric arrangement of suction and medicinal incorporating areas in an alternating pattern and which, upon being suction engaged in the manner described herein, facilitates the contact of the medicinal areas (or components shown at 16 and 18) in contact with the surface of the cervix 1.

Alternating with the annular shaped medicinal areas 16 and 18 are concentrically arrayed suction inducing/retaining zones 20, 22 and 24, a central-most vacuum aperture location 26 defining a rigid push-button depicted at an embedded underside of the general dome-shaped and suction inducing middle component 12. Without limitation, the medicinal impregnated or entrained areas 16 and 18 can incorporate any of a solid, gel or paste-like composition which, upon implantation within the patient and upon the exterior surface of the cervix or other organ, is time released over any desired period, such as in one non-limited application a two to four week period. As further previously described, the entrained medication can include any of an anti-cancer drug as well as any other type of medication or antibiotic such as designed to fight viral and/or bacterial infections or to assist in repairing of tears in the organ walls and/or surrounding ligamenture.

Figure 2:
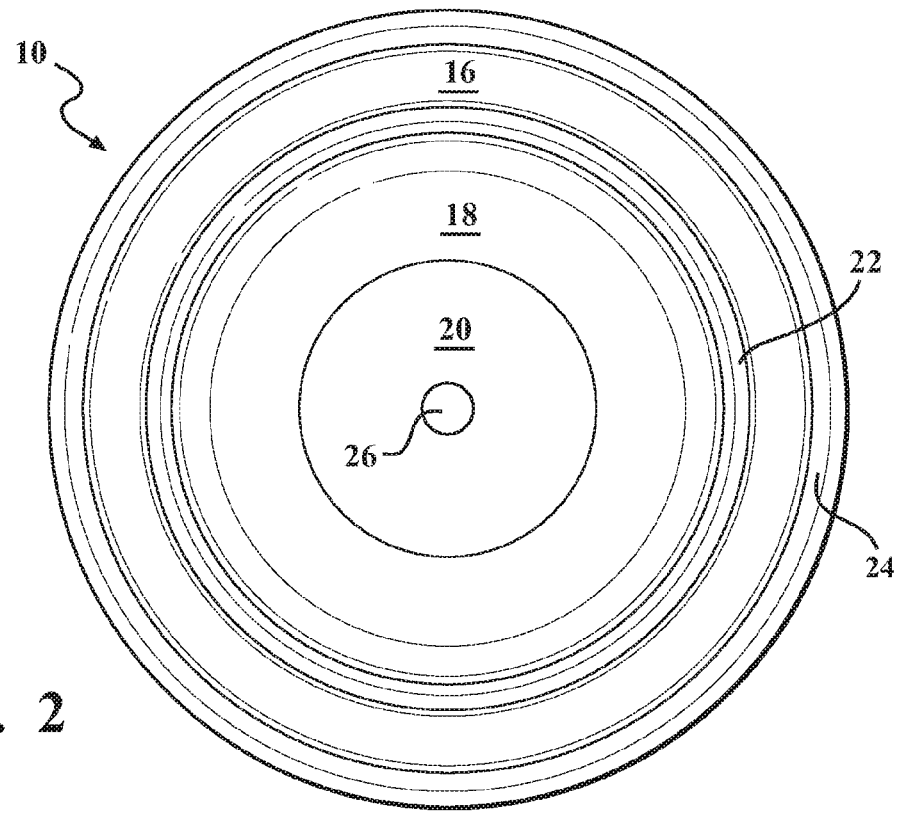
FIG. 2 is a rotated underside of the medicinal delivery device of FIG. 1 and which illustrates the concentrically arranged suction and medicinal incorporating components in contact with the surface of the organ.
Figure 3:
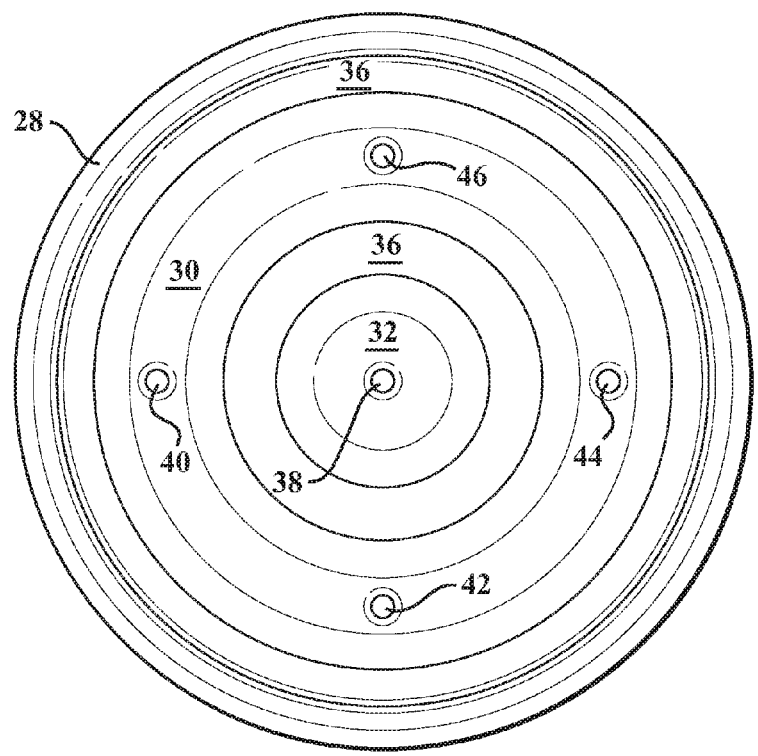
FIG. 3 is an illustration similar to FIG. 2 of an alternate underside configuration of a medicinal delivery device in which the suction generating areas exhibit a grooved profile.

Proceeding to FIG. 3, an illustration similar to FIG. 2 is shown of an alternate underside configuration of a medicinal delivery device in which the suction generating areas are reconfigured as shown at 28, 30 and 32 in alternating arrangement with suction inducing/retaining areas 34 and 36. As depicted, the suction generating areas 28-32 each exhibit a grooved profile and further include strategically placed vacuum apertures (at 38 for central-most suction area 32 as well as in circumferentially arrayed fashion at 40, 42, 44 and 46 dispersed along intermediate suction area 30).

Figure 4:
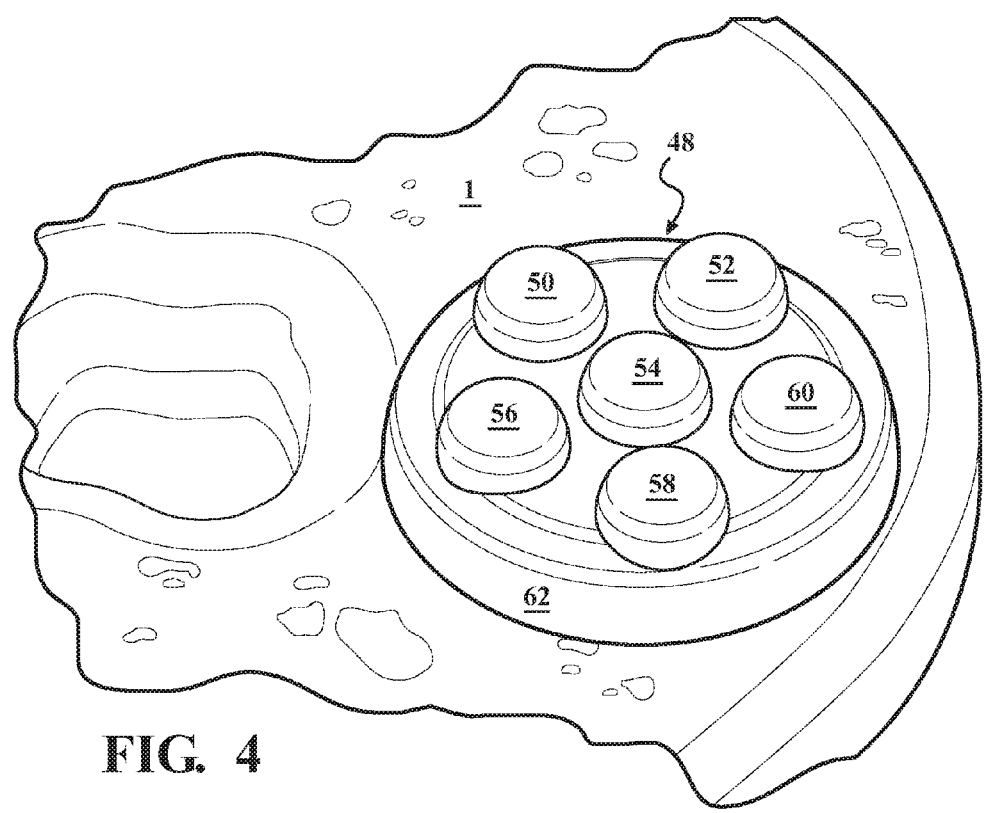
FIG. 4 is an upper side perspective similar to FIG. 1 of an alternate configuration of medicinal delivery device in which the single large suction pad is reconfigured as a plurality of smaller and individually suction generating pads.
Figure 5:
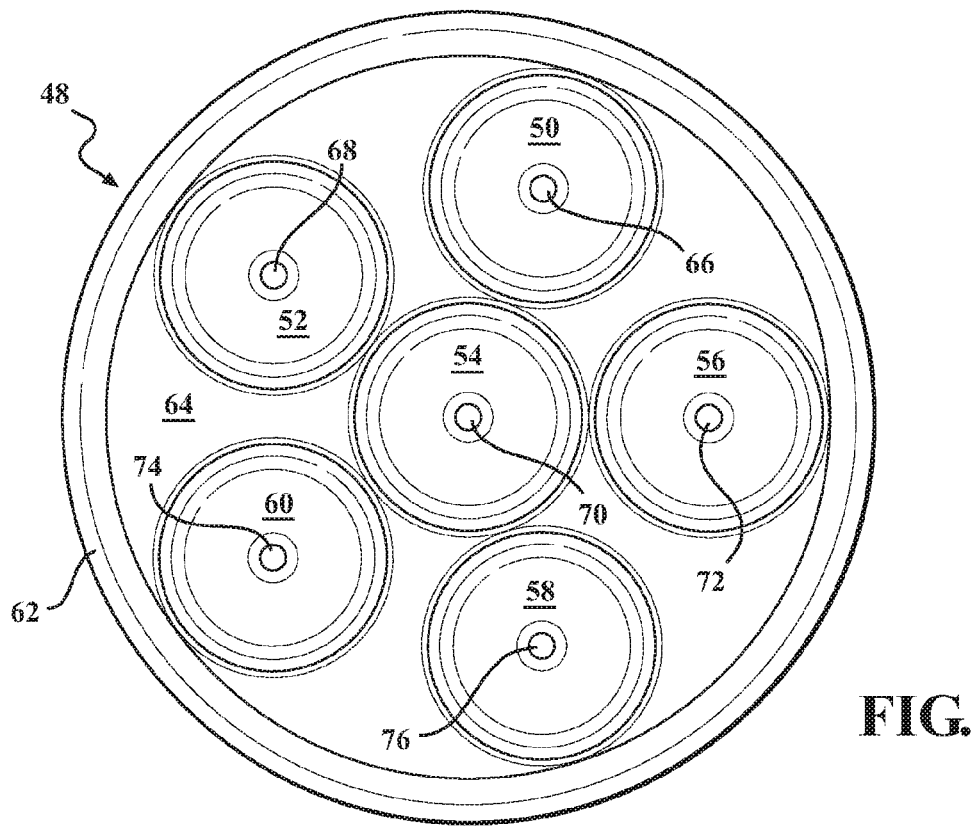
FIG. 5 is a rotated underside of the medicinal delivery device of FIG. 4 and which illustrates the arrangement of the medicinal delivery surface surrounding the individually placed suction pads.

FIG. 4 is an upper side perspective similar to FIG. 1 of an alternate configuration, generally at 48, of medicinal delivery device in which the single large suction pad is reconfigured as a plurality of smaller and individually suction generating pads 50, 52, 54, 56, 58 and 60 distributed along a generally dome shaped vacuum sealing plasticized body 62. FIG. 5 is a rotated underside of the medicinal delivery device of FIG. 4 and which again illustrates the interior configuration of the suction pads 50-60, along with the arrangement of the medicinal delivery surface 64 surrounding the individual dispersed suction pads and communicating with the underside perimeter edge of the dome shaped body 62. As further shown in FIG. 5, underside accessible apertures 66-76 are provided respectively for each of the individual suction pads 50-60 and which function in a similar manner as previously described for adhering to the moist exterior of the uterus, as shown in FIG. 4, and upon which the soft and deformable/collapsible and individual pads 50-60 being progressively depressed to create a multiple of individual contact locations for providing redundancy in adhering to the uterine surface while maintaining the medicinal delivery area 64 in continuous contact with the surface of the uterus or other desired organ 1.

Figure 6:
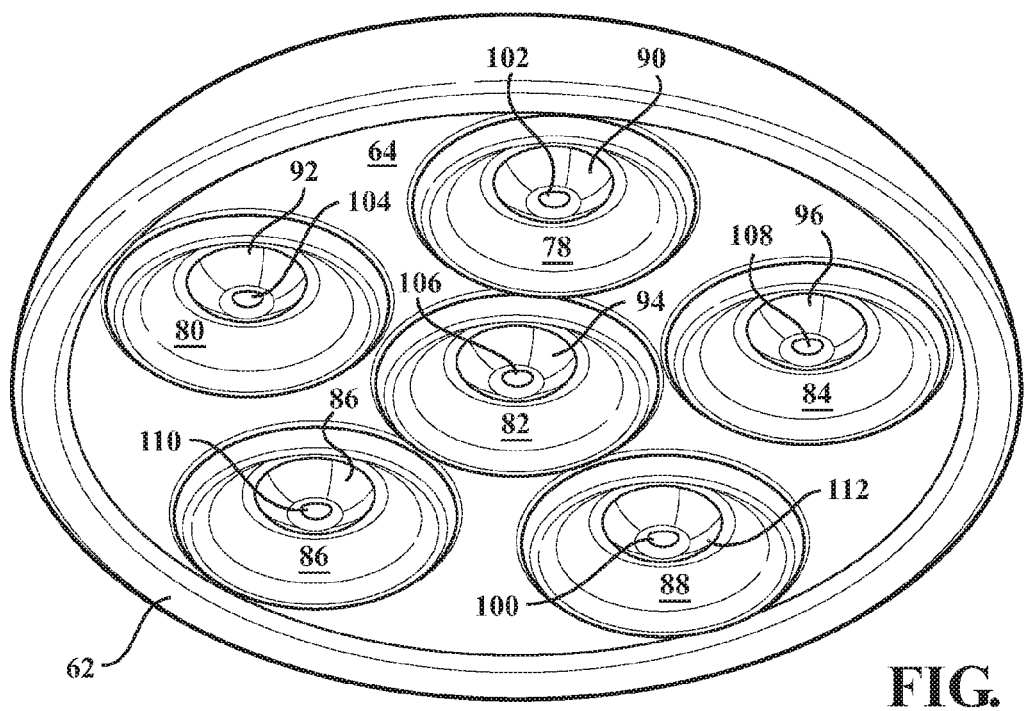
FIG. 6 is an underside perspective of a species variation of the embodiment generally shown in FIG. 5 and in which the individual suction pads are reconfigured with inner hemispherical underside projections to assist in suction generation.

Proceeding to FIG. 6, an underside perspective is shown of a species variation of the embodiment generally shown in FIG. 5, in which the dome shaped suction body 62 and underside medicinal delivery component 64 are identical to that in FIG. 5, and in which the individual suction pads are reconfigured as shown at 78-88, such that each includes an inner hemispherical underside projection 90-100 with an inner aperture 102-112 (mimicking a generally octopus tentacle like arrangement) to assist in suction generation. Beyond the configuration shown, it is understood that the individual suction generating areas can be reconfigured or redesigned in any of a number of non-limiting designs and which, upon depressing the soft outer dome 62, facilitate enhanced and secure adherence to the moist surface of the cervix (or other organ).

Figure 7:
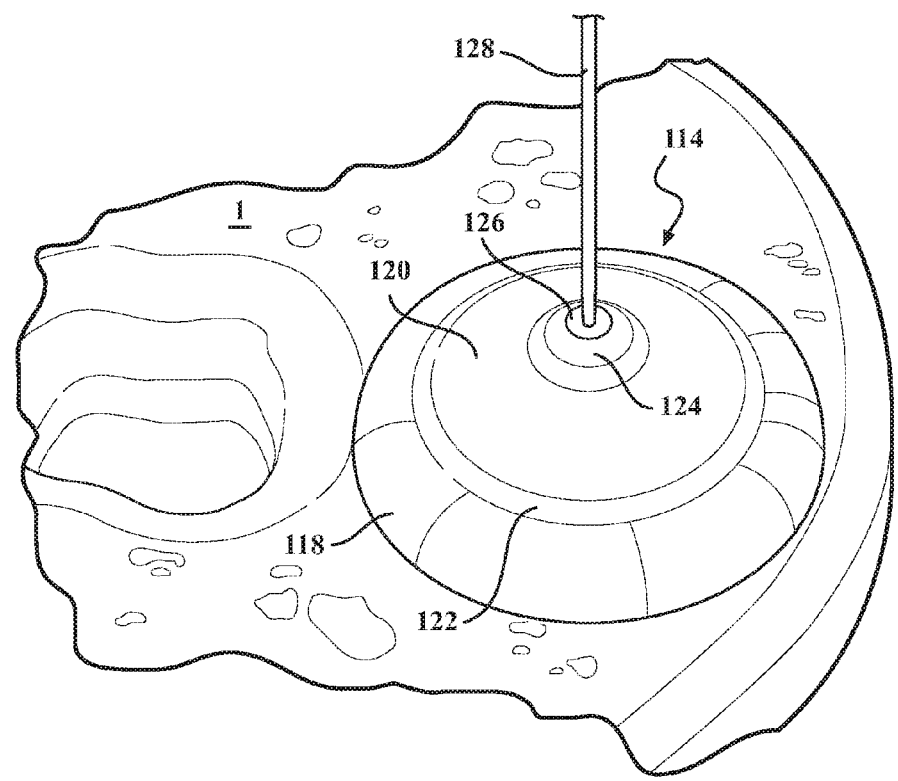
FIG. 7 is an illustration of an environmental perspective of a cervix attachable medicinal delivery device according to a yet further variant and in which a central nipple aperture formed into a soft sealing material receives a tip of an inserted needle in order to create a retaining suction with the uterine surface exterior.

FIG. 7 is an illustration of an environmental perspective, generally at 114, of a uterine attachable medicinal delivery device according to a yet further variant. The integral and dome shaped body is generally redesigned to include an outer-most skirt portion 118 and an intermediate portion 120 separated by a grooved annular boundary 122. An inner most raised or protuberance location 124 of the body exhibits a central nipple aperture formed into a soft sealing material 126 for receiving a tip of an inserted needle 128 in order to create a retaining suction with the cervix surface exterior.

Figure 8:
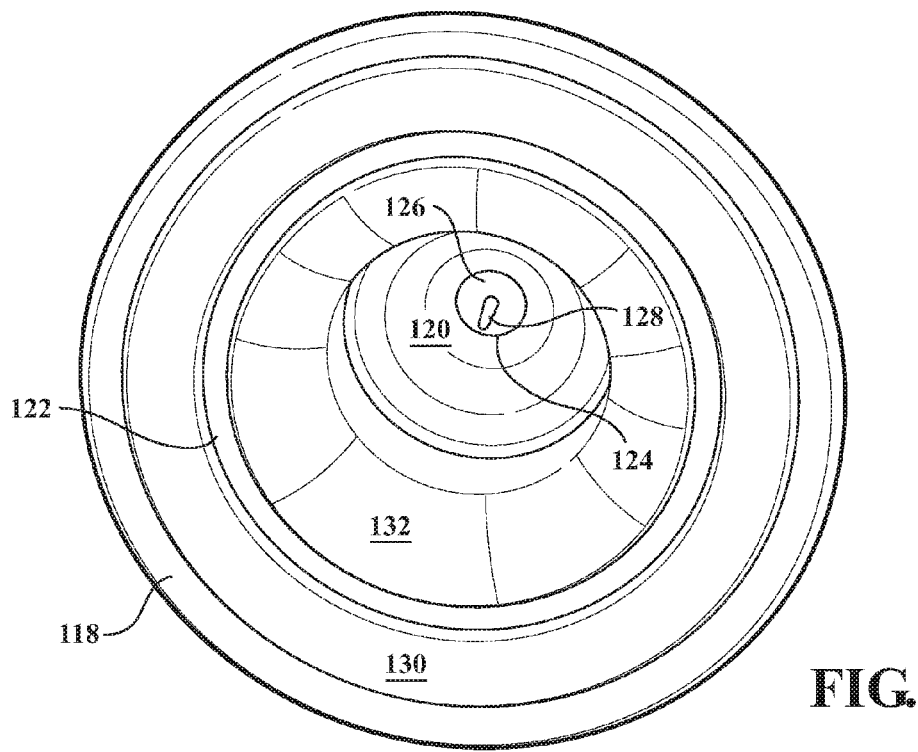
FIG. 8 is a rotated underside of the medicinal delivery device of FIG. 7 exhibiting a pattern generally identical to that depicted in FIG. 2, and with the needle tip evident from an exteriorly inserting location for generating the desired retaining suction within the underside interior for locating and holding the device in place upon the uterine exterior wall.

FIG. 8 is a rotated underside of the medicinal delivery device of FIG. 7 exhibiting a pattern generally identical to that depicted in FIG. 2, and in which the outer perimeter edge 118 extends to an underside lip of the body and which, combined with the intermediate annular grooved boundary 122, separates medicinal delivery areas 130 and 132 of a type and nature similar to that previously described. The medicinal delivery areas 130 and 132 are layered upon the underside locations of the dome shaped body as generally shown in FIG. 7 and further such that the needle tip 128 is evident from the exteriorly inserting location for generating the desired retaining suction within the underside interior for locating and holding the device in place upon the cervix exterior wall.

Figure 9:
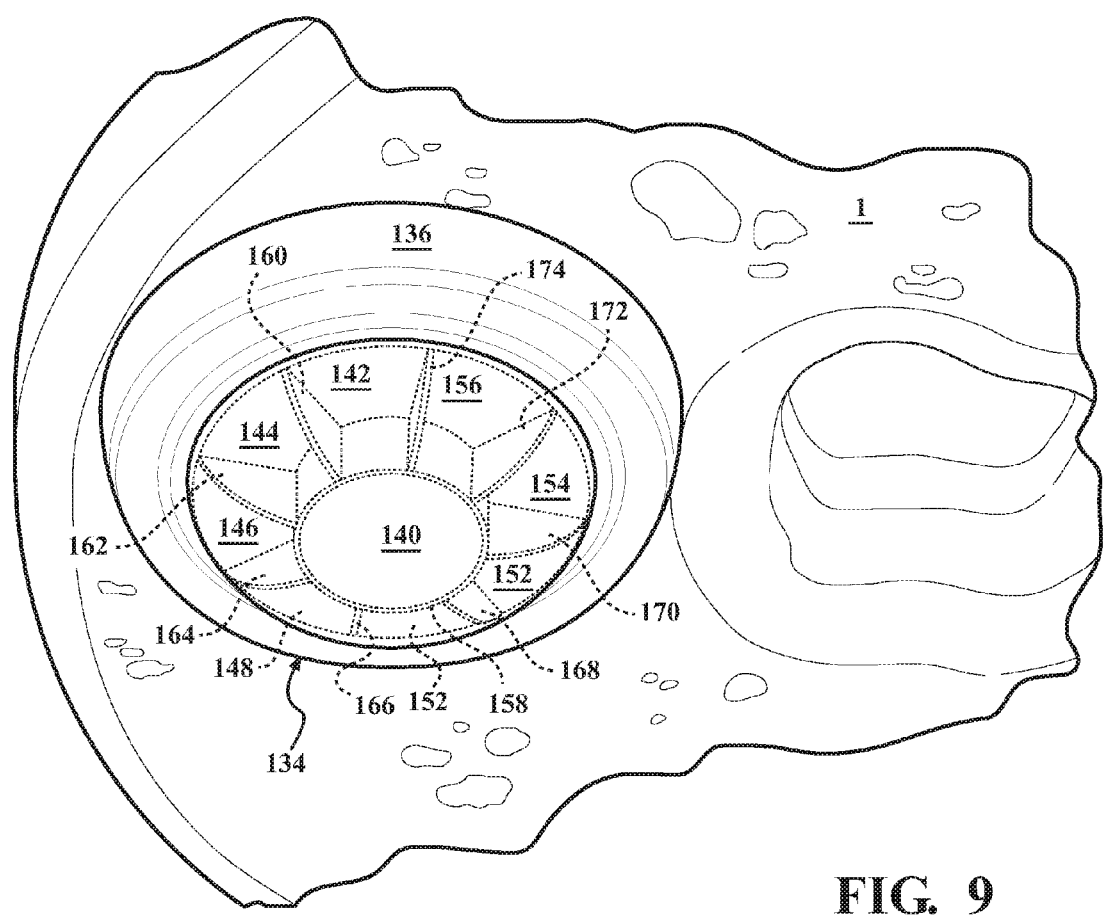
FIG. 9 is an environmental perspective of a medicinal delivery device according to a further variant attached to the uterine exterior and in which a central and inner suction inducing chamber is individually communicated to a plurality of outer and perimeter arranged vacuum chambers for generating the desired suction adhering effect.

FIG. 9 is an environmental perspective of a medicinal delivery device, generally at 134, according to a further variant attached to the cervix exterior 1. A generally dome shaped body is depicted at 136 terminating in a sealing lip underside 138 (see FIG. 10) which is similar to the previously described configurations and which assists in contact and vacuum adherence to the moist surface of the cervix or other desired organ.

A central area is depicted in substantially transparent fashion in FIG. 9 and includes a central and inner suction inducing chamber 140 which is individually communicated to each of a plurality of outer and perimeter arranged vacuum chambers 142-156 (these depicted as individual and generally trapezoidal shaped sub-chambers separated by an annular wall 158 defining the inner suction inducting chamber 140 and outer radial ribs 160-174 respectively separating the outer chambers 142-156. Each of the outer chambers 142-156 further includes a vacuum communicating aperture defined by an inner closed perimeter 176-190 associated with a base surface of each chamber separated by the projecting ribs.

Figure 10:
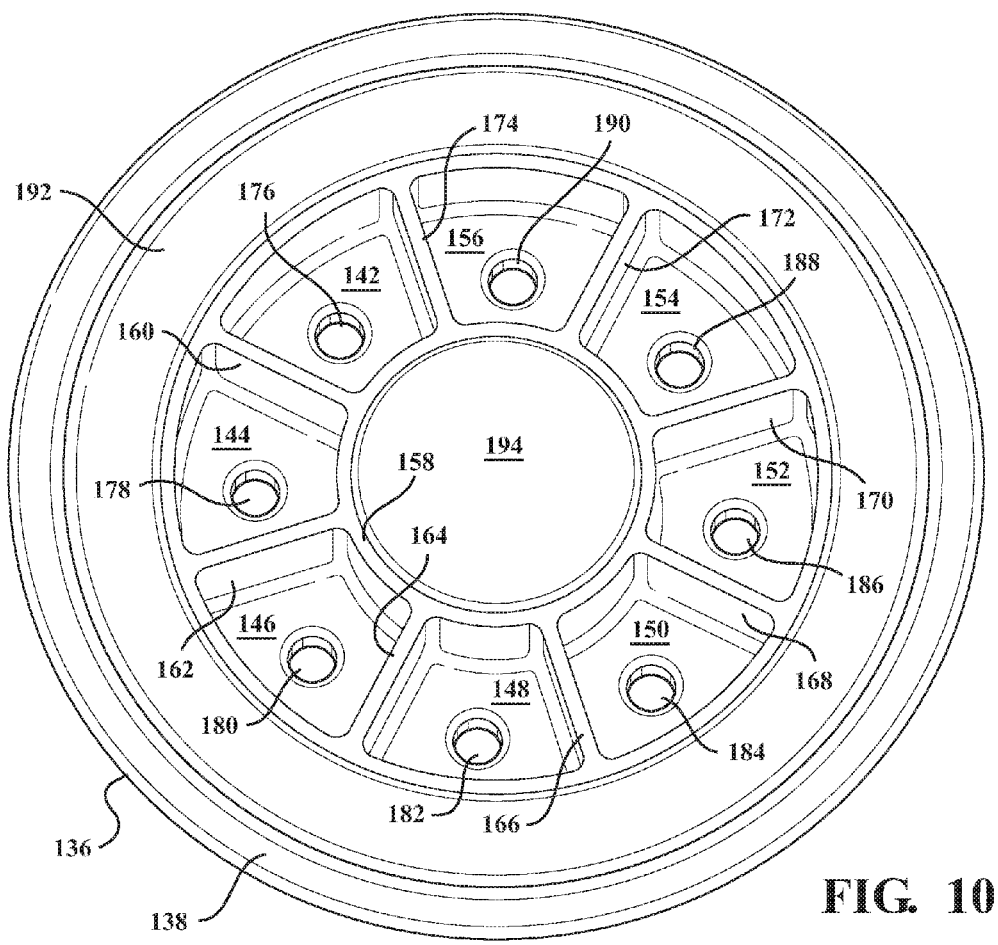
FIG. 10 is a rotated underside of the medicinal delivery device of FIG. 9 and which further illustrates the individual and generally trapezoidal shaped profile associated with each surrounding and circumferential/perimeter defined vacuum chambers along with showing the communicating apertures associated with each outer chamber for communicating the suction effects of the central chamber to the individual outer chambers.

As previously described, the desired suction effect results from the exterior dome shaped body 136 being collapsed, via the interior or central chamber 140, to issue airflow through each of the apertures (such as each of which can include one-way valves), with the reverse incentive of the body 136 to reform to its original three dimensional shape being opposed by the vacuum created effects within each of the outer chambers and in order to drawn into open undersides of each outer chamber 142-156 moistened surface locations of the cervix wall to establish the desired vacuum adherence in like multiple/redundant fashion. Also depicted in FIG. 10 is a first and generally outer and annular shaped medicinal delivery layer 192 interposed between an inner extending edge of the underside lip 138 and the dome shaped body 136, combined with an inner most medicinal delivery layer or area 194 which closes off the central chamber 140, the medicinal layers both configured and operational in a manner as previously described for facilitating in time release delivery of a desired entrained medicinal composition in surface applied fashion to the desired organ via its moistened exterior.

Figure 11:
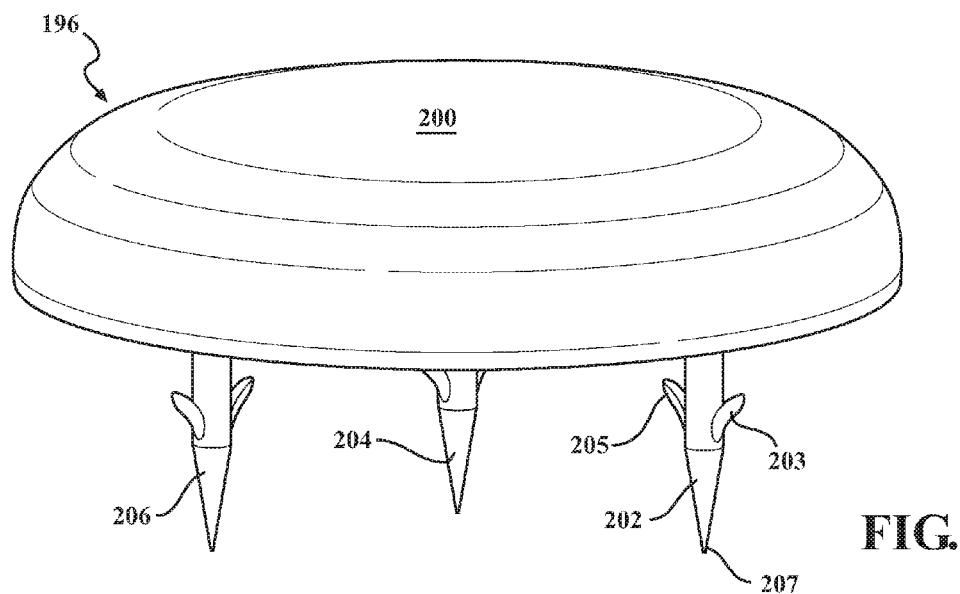
FIG. 11 is a perspective view of a medicinal delivery device according to a further variant and in which the suction generating aspects are substituted by underside projecting prongs for engaging within the uterine wall.

FIG. 11 is a perspective view, generally at 198, of a medicinal delivery device according to a further variant which includes a modified and generally three dimensional shaped body 200 in which the suction generating aspects are substituted by underside projecting prongs 202-210 (see also FIG. 12 underside) for engaging or piercing through the outer layers associated with the cervix or other organ wall. As shown, the prongs 202-210 each include intermediate angled winglets, for example depicted at 203 and 205 for selected prong 202 and which further terminates in a pointed end 207.

Figure 12:
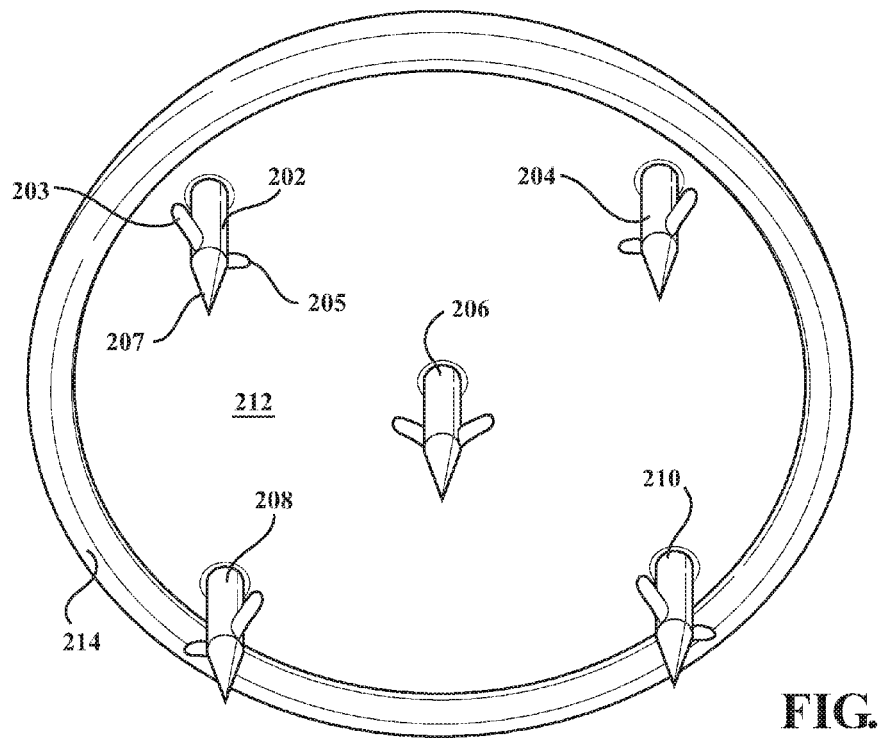
FIG. 12 is an underside perspective of the medicinal delivery device of FIG. 11 and in which a substantially flattened and disc shaped internal layer, through which the individual prongs project, comprises the medication delivery component.

As further depicted from the underside of FIG. 12, a substantially flattened and disc shaped internal layer is shown at 212 which again comprises the medicinal delivery component and which extends to an underside lip 214 associated with the body 200, as well as through which the individual prongs project. Without limitation, other mechanical attachment mechanism can be substituted for that shown and which can operate according to any desired fashion for securing the device to the desired exterior location of the organ.

Figure 13A:
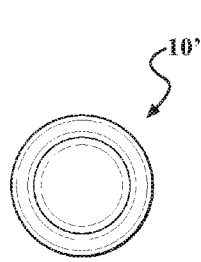
FIGS. 13A-13C are representative illustrations of different sized medicinal delivery devices adapted for implantation according to the present inventions.
Figure 13B:
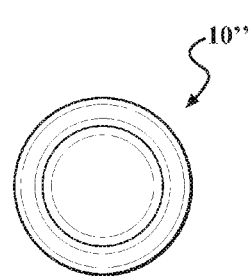
Figure 13C:
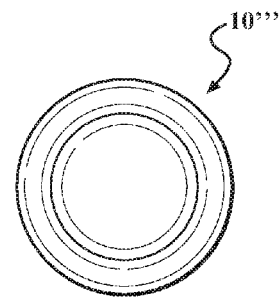

FIGS. 13A-13C are representative illustrations of different sized medicinal delivery devices, such as respectively depicted at each of 10', 10" and 10'" consistent with the initial disclosed variant, and which are adapted for implantation according to the present inventions according to any desired plural scale or arrangement. It is worth noting that the delivery devices not limited to the several examples disclosed can be provided in any number and/or size for addressing a given internal organ condition and in which a desired surface application of medicine is achieved through a specified placement pattern or protocol.

Referring now to FIG. 14, a perspective illustration is generally shown at 216 of an insertion tool for delivery and implanting a medicinal delivery device such as according to any of the prior variants disclosed (depicted generally in plan cutaway at 218) and which can be provided as any of a system, combination or kit. Features associated with the tool 216 (such as which can include a medical grade steel or sanitary plastic) include an elongated body 220 separating a bulbous (handling and gripping) end 222 and a forward most located in situ delivery end 224. Without limitation, the shaping of the tool is not limited to that depicted herein and can include other shapes and sizes as reflective of the skill of one in the relevant art.

As further shown, the non-limiting depiction of the forward delivery end 224 is exhibited by a generally cylindrical profile which generally matches the cross sectional profile of the medicinal delivery device 218. As further best shown in FIG. 14, a plurality (such as four) of perimeter located and arcuate profile clamps 226, 228, 230 and 232 are exhibited about the exposed facing circumference of the delivery end 224 of the tool, these configured as will be further described below for gripping circumferential perimeter locations of the medicinal delivery device 218 as shown in each of FIGS. 14-17.

Figure 17:
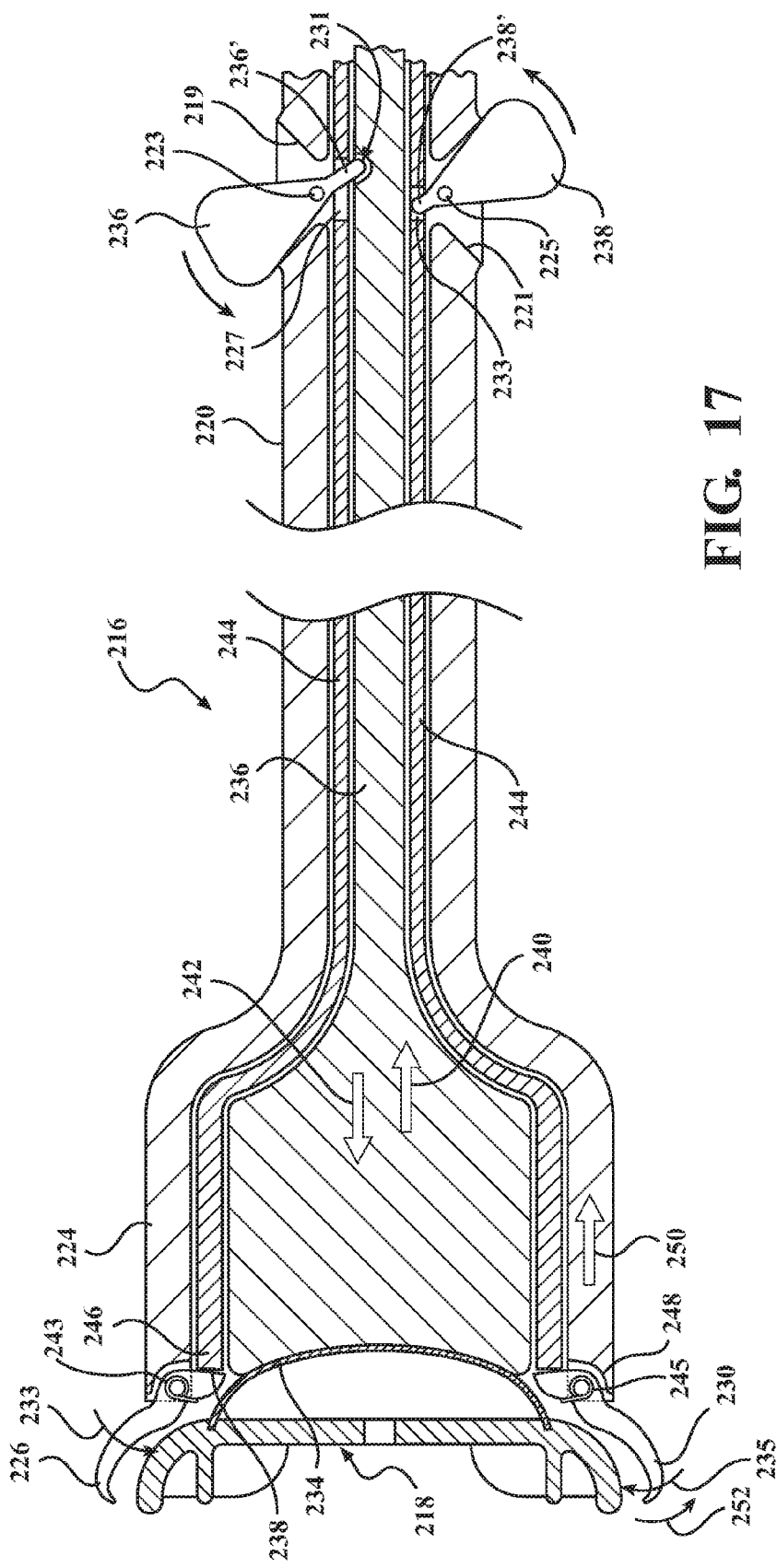
FIG. 17 is an enlarged, reduced length and longitudinal cutaway view of the tool of FIG. 15 better depicting the substructure for accomplishing both perimeter clamp and vacuum release of the medicinal delivery device.

As partially depicted in each of FIGS. 15 and 16, and as further best shown in longitudinally cutaway FIG. 17, an upper most arcuate surface 234 of the medicinal delivery device 218 exhibits vacuum adhering aspects as influenced by the interior geometry of the tool, such as which helps to maintain a vacuum force exerted by the tool on the delivery device 218 in a first clamping/vacuum gripping configuration. A two part trigger mechanism is further depicted by toggle portions 236 and 238 proximately located relative to one another at a remote location of the stem 220.

As will be described in further detail in FIG. 17, FIG. 15 depicts the clamping and vacuum adhering aspects of the tool, whereas FIG. 16 further shows the simultaneous outward release of the clamps 226-232 (see associated directional arrows) concurrent with release of the suction force exerted on the upper most flexible surface 234 associated with the delivery device 218, at which point the delivery device is released from the inserting end 224 of the tool and permitted to be implanted at the desired in situ location of the patient.

FIG. 17 is an enlarged, reduced length and longitudinal cutaway view of the tool 216 of FIG. 15 better depicting the structure for accomplishing both perimeter clamp and vacuum release of the medicinal delivery device. As shown, this includes the toggle 236 being rotated in clockwise fashion as shown in FIG. 15 in order to manipulate an interior displaceable stem 237 with forward depicted concave profile 241 for inducing a suction force upon the flexible exterior convex surface 234 of the delivery device 218.

The clamps (see as shown at 226 and 230 in FIG. 17) each include a coil spring or other biasing mechanism situated at the pivot point (further at 243 and 245) at which each of the clamps are biased in an inwardly pivoting fashion (see further arrows 233 and 235) in order to engage the outer lip edge of the device 218. Following manipulation of the first toggle 236 resulting in forward displacement of the stem 237 and implantation of the device 218, a second toggle 238 in the longitudinal cutaway of FIG. 17 is pivoted as shown to rearwardly displace a forward engaging end 246 of the inner coaxial sleeve 244 in the direction 240 and in order to retract the coaxial sleeve 244 surrounding the stem 237 and to displace the clamps 226, 228, 230 and 232 outwardly against their spring bias 243 and 245 out of engagement with the outer lip edge of the device 218. Toggle 236 is manipulated to extend or retract the inner stem 237 only along either opposite directions 240 and 242. Toggle 238 is manipulated to displace both the stem 237 and outer sleeve 244 in the direction of arrow 242, and the sleeve 244 only in the direction of arrow 240 (the first toggle 236 being pivoted to separately retract the stem 237 and forward concave support surface 234.

As again shown in FIG. 17, the coaxial sleeve 244 encircles the inner displaceable stem 237. A pair of upper and lower ramped apertures 219 and 221 are formed in the body 220 (FIG. 17) and the toggles 236 and 238 are crosswise pivotally secured (at 223 and 225) to the body there within as shown in cutaway and so that inwardly projecting portions 236' and 238' of the toggles can be pivoted to provide the above described motions of the coaxial sleeve 244 and inner stem 237. A slot 227 is formed in the coaxial sleeve aligning with aperture 219 and so that the projecting inner portion 236' of the toggle 236 directly engages an engagement recess 231 of the inner stem 237 positioned inside the slot 227. A further smaller sized slot 233 in the sleeve 244 is abutted by an inwardly projecting portion 238' of the second toggle for permitting displacement of the coaxially supported sleeve 244 in the rearwardly displacing direction of arrow 240, from a forward displaced position, and without again causing the inner stem 237 to concurrently rearwardly displace from the forward concave support surface 234 (without separately pivoting the first toggle 236 in the direction of the associated directional arrow in FIG. 17). In this fashion, separate inducement of the toggle portions 236 and 238 causes the toggle portions to abut the ramped edges of the outer body 220 in a manner which laterally displaces the inner stem 237 and coaxial sleeve 244 in the directions as referenced by bidirectional arrows 240 and 242 and as described above and in order to position and release the medicinal delivery device in a first implantation operation, the clamps again being outwardly pivoted by the trigger or toggle 238 in a retrieval operation prior to positioning about the implanted device and the trigger being oppositely manipulated to retracted the sleeve 237 and to cause the clamps to inwardly close to grip the medicinal delivery device during retrieval from the tissue or membrane lining of the organ.

Without limitation, a number of fulcrum or pivotal actuating structures can be integrated into the tool geometry which cause the necessary pivotal actuation of the clamps 226-232 in the desired fashion depicted, this in response to actuation of the toggle 238.

Figure 18:
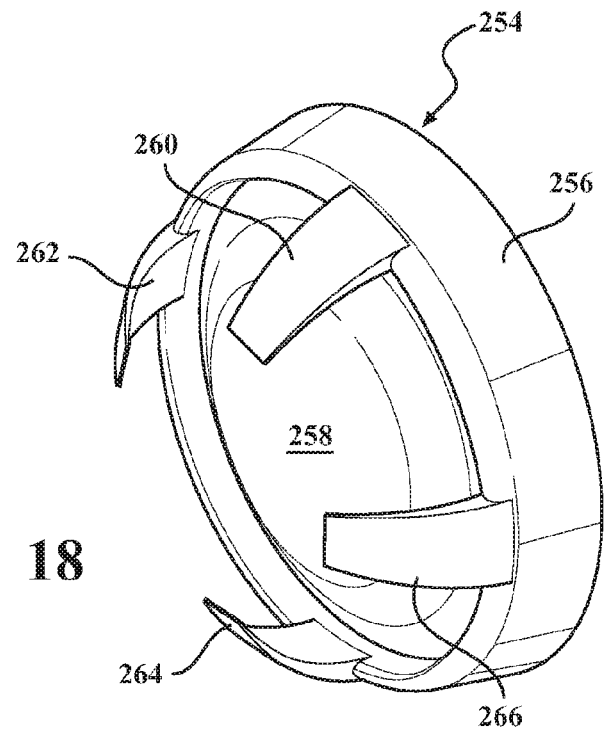
FIG. 18 is a front perspective view of an implantable medicinal delivery device according to a further embodiment exhibiting outer perimeter configured and movable gripping portions for engaging an in situ implantation location.

Referring to FIG. 18, a front perspective view is generally shown at 254 of an implantable medicinal delivery device according to a further embodiment and which exhibits an outer perimeter (generally annulus shaped) body 256 having a semi-flexible and semi-rigid configuration for implantation and subsequent removal to and from the patient. The body 256 contains a medicinal delivery component 258. A further plurality of perimeter configured and movable gripping portions are depicted at 260, 262, 264 and 266, these each further shown by blade edged outer tab locations as best shown in FIG. 18 which are configurable for engaging an in situ implantation location within the patient.

Figure 19:
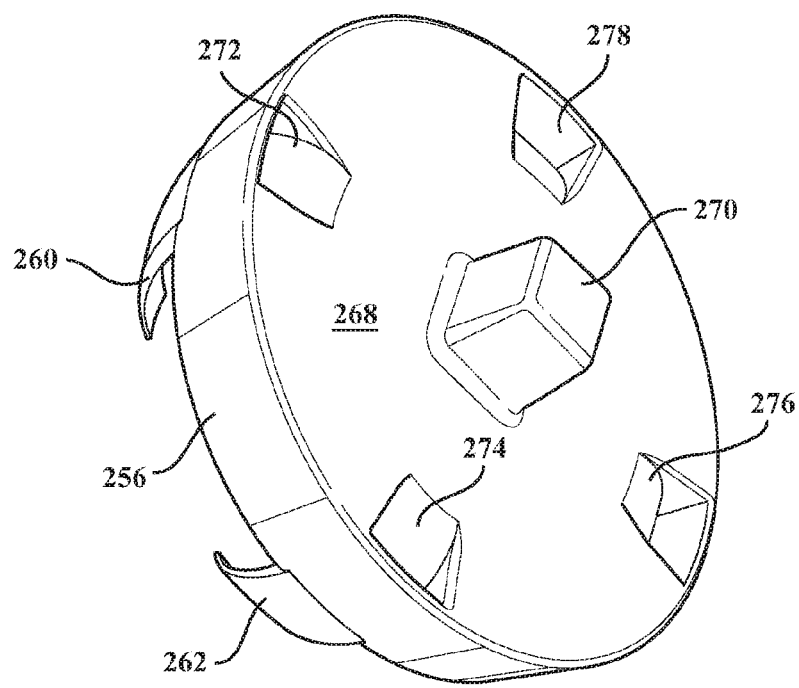
FIG. 19 is a rotated rear perspective view of the delivery device shown in FIG. 18 and depicting a plurality of outer perimeter insertion tool locations which align and communicate with the forward extending gripping portions.

FIG. 19 is a rotated rear perspective view of the delivery device 254 shown in FIG. 18 which includes a rear surface 268 associated annular shaped body 256, along with a central and rearward projecting/tool gripping post 270. A further plurality of outer perimeter insertion tool locations 272, 274, 276 and 278 correspond in alignment and communication with inner pocket locations defined in each of the gripping portions 260, 262, 264, and 266.

Figure 20:
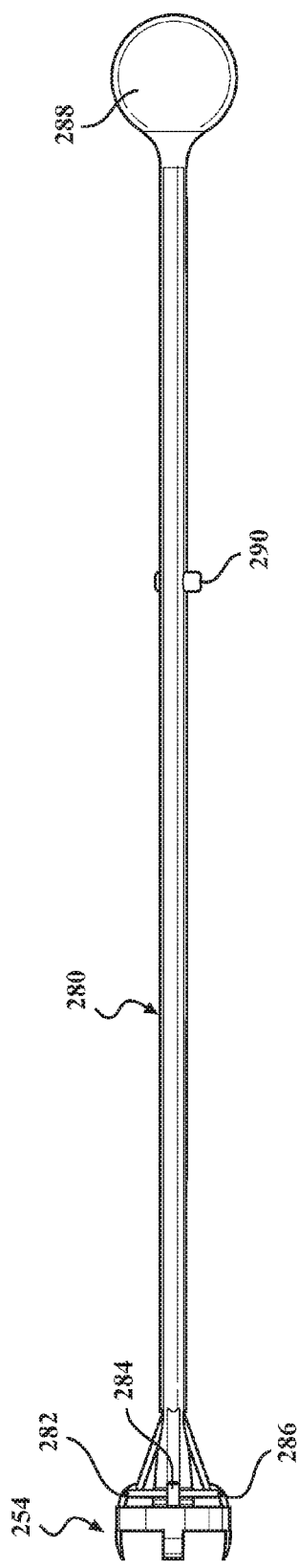
FIG. 20 is a plan view of the medicinal delivery device of FIG. 18 in use with a modified and inserting delivery tool in which a forward engaging configuration of the tool exhibited by multiple gripping fingers both aligns with and seats within the back surface located insertion tool locators associated with the delivery device in a first open position associated with the perimeter located device gripping portions.

FIG. 20 is a plan view of the medicinal delivery device 254 of FIG. 18 in use with a modified and inserting delivery tool, generally at 280, and in which a forward engaging configuration of the tool is exhibited by multiple and circumferentially offset gripping fingers, these shown by gripping fingers 282, 284 and 286 associated with gripping portions 260, 264 and 266, with a fourth gripping finger not shown which aligns and rearwardly engages additional gripping finger 262. As further depicted in FIG. 20, the tool 280 includes a bulbous handling profile 288 and an intermediate stem located trigger 290 in a first open location in which the gripping fingers of the tool are seated rearwardly into contact with the interior communicating pockets of the gripping portions 260-266 in a first open/non-engaging position.

Figure 21:
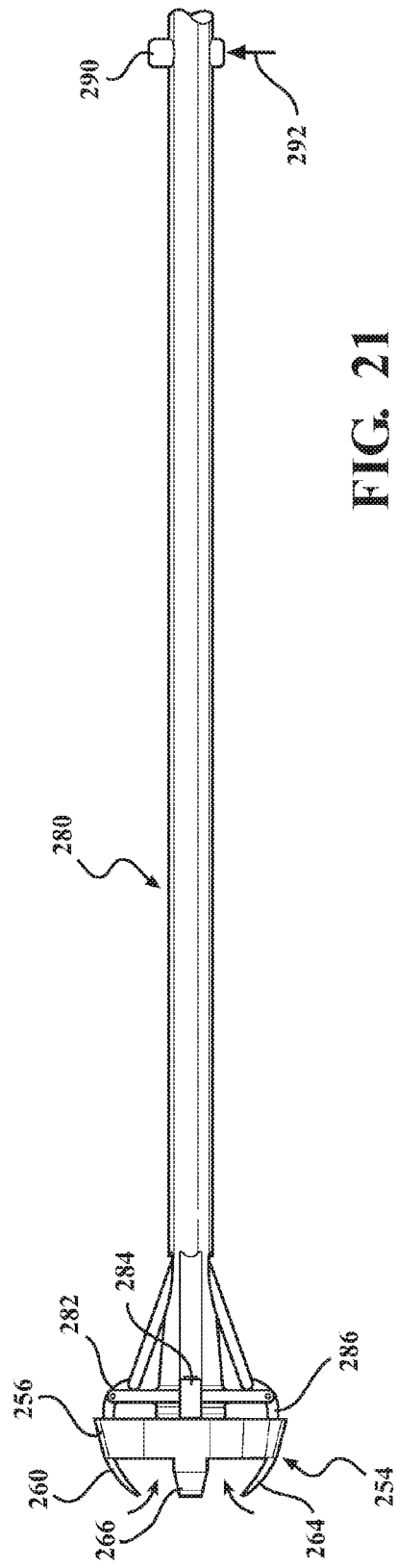
FIG. 21 is a succeeding view to FIG. 20 in which a trigger clamp configured at a stem extending location of the tool results in the inward actuation of the end disposed gripping fingers, as well as concurrent inward actuation of the controlled gripping portions for implanting the delivery device in situ within the patient.

Proceeding to FIG. 21, trigger 290 is depicted as actuated in a direction 292, this in order to actuate the gripping fingers 282-286 and associated gripping portions 260-266 in order to inwardly deflect the gripping portions in order to grab onto and retain contact with an associated implantation location of the patient (such as associated with an organ location in situ a cancerous growth or other tumor). Given the material construction of the outer annular portion of the delivery device as well as the gripping fingers, this can include either piercing the outer skin of the tumor or otherwise embedding into the tumor and subsequently deflecting the outer circumferential gripping portions in a manner which ensures location maintenance for the time period between an initial implantation and subsequent removal, such as which again uses the installation tool described herein.

Figure 22:
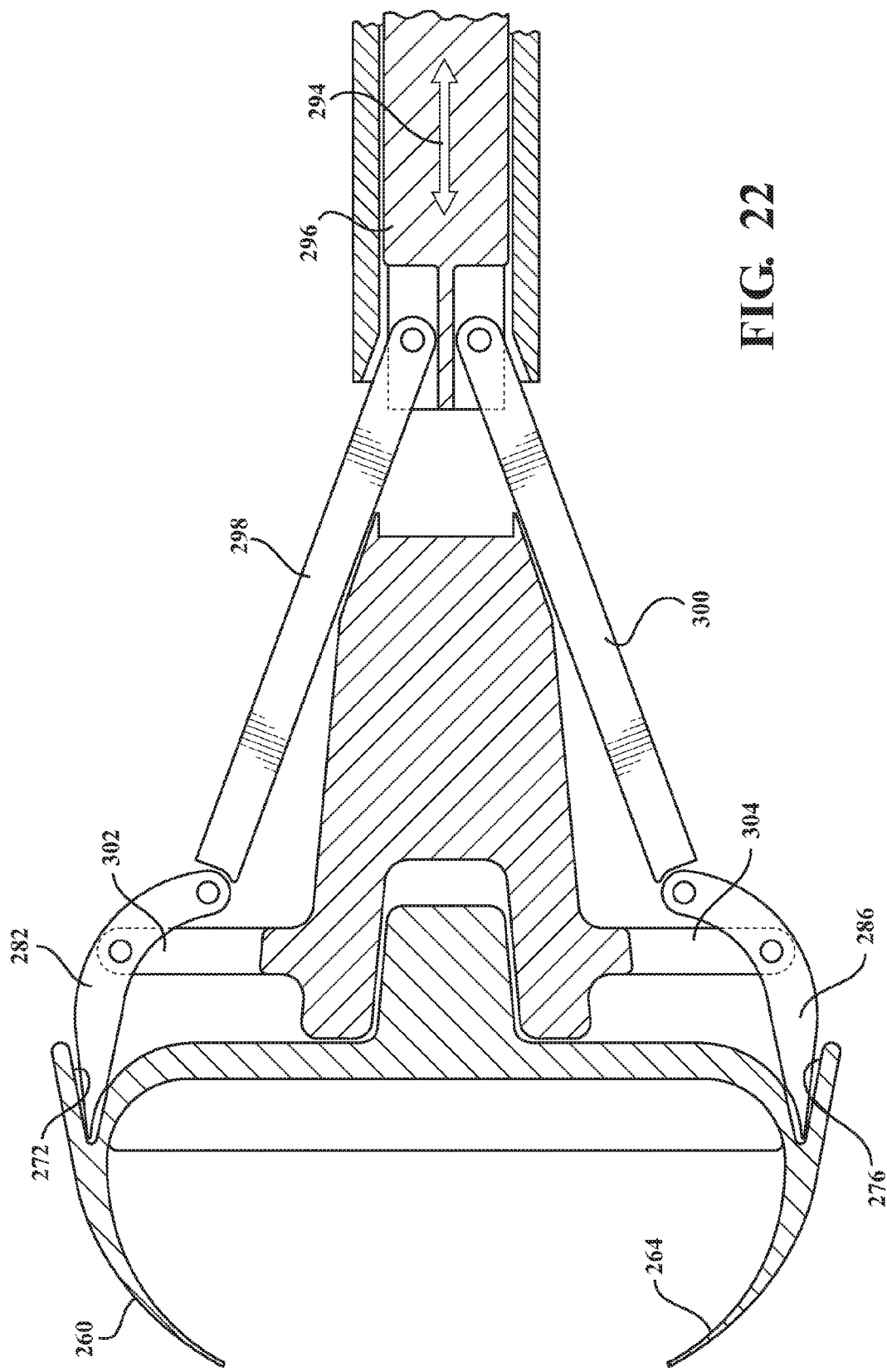
FIG. 22 is an enlarged delivery end and longitudinal cutaway view of the tool of FIG. 20 and which better depicts the inter-actuating linkages for controlling the gripping fingers in engagement with the medicinal delivery device.

FIG. 22 is an enlarged delivery end and longitudinal cutaway view of the tool of FIG. 20 and which better depicts the inter-actuating linkages for controlling selected illustrated gripping fingers 282 and 286 in engagement with the recessed engaging locations 272 and 276 medicinal delivery device. This includes multi-directional (see arrow 294) actuating stem 296, this connected through a fulcrum linkage to the trigger 290 in such a fashion as to pivotally actuate forward angled inter-linkages 298 and 300 extending from rearward locations to a forward displaceable end of the stem 296 to rearward linkage engagement locations with the selected gripping fingers 282 and 286.

The gripping fingers are in turn mounted to inner fixed pedestal supports (see further at 302 and 304) and which, upon actuating the stem 296 in a rearward displaceable direction causes the gripping portions 260-266 to bite inwardly. Subsequent forward displacement of the inner stem 296 of the tool in turn results in counter pivoting of the gripping portions to outwardly displace or release from the organ or tissue implantation location.

FIG. 23 is an illustration of a modified inserting end of an installation tool such as similar to that depicted in FIG. 20 and in which a high intensity light source, see as depicted by dome shaped element 306 not limited to an LCD, LED or other portable and high intensity emitting element, is integrated into the tool proximate the forward implantation end. This is further depicted by a seating location 380 which is mounted atop a narrowed cross sectional bridge 310 in order to be situated at an elevated location and minimally visibly obtrusive fashion while remaining proximate to the medicinal delivery location and in order to facilitate correct location and delivery of the medicinal delivery device. Associated illumination structure, including a portable battery or other power source, can be integrated into the tool for operating the light 306, such as which can be actuated on/off by a suitably located switch.

Having described my invention, other and additional preferred embodiments will become apparent to those skilled in the art to which it pertains, and without deviating from the scope of the appended claims. This can include the medicinal delivery device according to any of the previously disclosed variants, further being adapted to engagement with any other human and/or mammalian type internal organ, not limited to bowels, kidney, liver, lungs, and the like.

We claim:

1. A tool for implanting and removing a medicinal delivery device, the device having an arcuate body with an adhering underside, said tool comprising:

an elongated body having a perimeter defining forward end;

a plurality of clamps extending from circumferentially locations of said perimeter defining forward end such that said clamps are supported upon and around said forward end apart from an interior of said body, said clamps adapted to grip perimeter locations of the medicinal delivery device prior to implantation;

an actuating mechanism of said body operable by a trigger for outwardly pivoting said clamps in an implanting operation for releasing the medicinal delivery device during attachment of the device to a tissue or membrane lining of an internal organ, said clamps being outwardly pivoted by said trigger in a retrieval operation prior to positioning about the implanted device, said trigger being further manipulated to cause said clamps to inwardly grip the medicinal delivery device during retrieval from the tissue or membrane lining of the organ;

said actuating mechanism further comprising a stem terminating in a flexible concave end face exposed at said forward end so that said concave end face is surrounded by said circumferentially arrayed clamps, said flexible end face adapted to supporting the medicinal delivery device in combination with said clamps;

a sleeve coaxially supported inside the body and around said stern, forward displacement of said sleeve engaging and outwardly pivoting said clamps; and said trigger further comprising a first toggle for displacing said inner stem forwardly independently of said sleeve to advance said concave face, said trigger including a second toggle for retracting said sleeve independently of said stem in order to release said clamps.

2. The tool as described in claim 1, said elongate body further comprising a rearward bulbous shaped end.

3. The tool as described in claim 1, further comprising said body having a shape and size and being constructed of either of a medical grade steel or sanitary plastic.

4. The tool as described in claim 1, said clamps each further comprising a spring loaded portion pivotally secured to an annular forward edge of said forward end.

5. The tool as described in claim 1, further comprising an illuminating light source supported on said body.

* * * * *